(12) United States Patent
Tathireddy et al.

(10) Patent No.: US 11,931,138 B2
(45) Date of Patent: Mar. 19, 2024

(54) HYDROGEL SENSOR ASSEMBLY (71) Applicant: Applied Biosensors, LLC, Salt Lake City, UT (US)

(72) Inventors: Prashant Tathireddy, Salt Lake City, UT (US); Rohit Sharma, Salt Lake City, UT (US); Seung Hei Cho, Salt Lake City, UT (US); Nicholas Frazier, Salt Lake City, UT (US); Yoonsung Goo, Salt Lake City, UT (US)

(73) Assignee: Applied Biosensors, LLC, Salt Lake City, UT (US)

( * ) Notice: Subject to any disclaimer, the term of this patent is extended or adjusted under 35 U.S.C. 154(b) by 1496 days.

(21) Appl. No.: 16/221,003

(22) Filed: Dec. 14, 2018

(65) Prior Publication Data

US 2019/0231218 A1   Aug. 1, 2019

Related U.S. Application Data

(60) Provisional application No. 62/598,785, filed on Dec. 14, 2017.

(51) Int. Cl.
*A61B 5/06* (2006.01)
*C08J 3/075* (2006.01)
(Continued)

(52) U.S. Cl.
CPC .............. *A61B 5/06* (2013.01); *C08J 3/075* (2013.01); *C08J 3/24* (2013.01); *C08L 33/04* (2013.01); *G01N 27/72* (2013.01); *G01N 33/00* (2013.01); *A61B 2562/04* (2013.01); *A61B 2562/16* (2013.01)

(58) Field of Classification Search
CPC ... A61B 5/06; A61B 2562/04; A61B 2562/16; C08J 3/075; C08J 3/24; C08L 33/04; G01N 27/72; G01N 33/00; G01B 7/24
See application file for complete search history.

(56) References Cited

U.S. PATENT DOCUMENTS 6,398,562 B1    6/2002 Butler et al.
6,488,872 B1 *  12/2002 Beebe ............... B01L 3/502738
                                                    264/254
(Continued)

FOREIGN PATENT DOCUMENTS

WO   WO 2010/075115 A2   7/2010
WO   WO 2014/116179 A1   7/2014

OTHER PUBLICATIONS

Rizwan et al.; "pH Sensitive Hydrogels in Drug Delivery: Brief History, Properties, Swelling, and Release Mechanism, Material Selection and Applications;" Polymers; (Apr. 12, 2017); pp. 137; vol. 9, Issue 4; <doi: 10.3390/polym9040137 >.

(Continued)

*Primary Examiner* — Baisakhi Roy
*Assistant Examiner* — Kaitlyn E Sebastian
(74) *Attorney, Agent, or Firm* — Thorpe North & Western, LLP.

(57) ABSTRACT

A hydrogel sensor device can include a crosslinked hydrogel body which changes in volume in response to an environmental stimulus, a support post positioned to mechanically support the crosslinked hydrogel body during the change in volume, and a sensor positioned to detect the change in volume in the crosslinked hydrogel body.

21 Claims, 9 Drawing Sheets

(51) Int. Cl.
*C08J 3/24* (2006.01)
*C08L 33/04* (2006.01)
*G01N 27/72* (2006.01)
*G01N 33/00* (2006.01)

(56) References Cited

U.S. PATENT DOCUMENTS

| | | |
|---|---|---|
| 6,751,491 B2 | 6/2004 | Lew et al. |
| 6,780,647 B2 | 8/2004 | Fujiwara et al. |
| 7,713,736 B2 | 5/2010 | Beebe et al. |
| 8,840,839 B2 | 9/2014 | Iordanov et al. |
| 9,042,954 B2 | 5/2015 | Bommakanti et al. |
| 9,694,338 B2 | 7/2017 | Murphy et al. |
| 9,999,369 B2 | 6/2018 | Ziaie et al. |
| 10,073,346 B2 | 9/2018 | Hribar et al. |
| 2002/0155425 A1* | 10/2002 | Han .................... G01N 33/66 435/14 |
| 2006/0227330 A1* | 10/2006 | Hjelme ............... G01N 21/7703 356/481 |
| 2009/0170209 A1 | 7/2009 | Machauf et al. |
| 2009/0302498 A1 | 12/2009 | Nedestam |
| 2010/0100183 A1* | 4/2010 | Prewett ............... A61B 17/7068 623/17.11 |
| 2016/0015323 A1* | 1/2016 | Tathireddy .......... A61B 5/14532 600/585 |
| 2016/0215253 A1 | 7/2016 | Bhola et al. |
| 2016/0349162 A1* | 12/2016 | Ebert ..................... G01N 15/06 |
| 2018/0153453 A1 | 6/2018 | Bunge et al. |
| 2018/0228428 A1 | 8/2018 | Anker et al. |

OTHER PUBLICATIONS

Zhang et al.; "Hydrogel-Based Glucose Sensors: Effects of Phenylboronic Acid Chemical Structure on Response;" Chemistry of Materials; (2013); pp. 3239-3250; vol. 25, Issue 15; <doi: 10.1021/cm401738p >.

* cited by examiner

HYDROGEL SENSOR ASSEMBLY

RELATED APPLICATION

This application claims the benefit of U.S. Provisional Patent Application No. 62/598,785, filed on Dec. 14, 2017, which is incorporated herein by reference.

GOVERNMENT INTEREST

This invention was made with government support under SBIR Phase 1 Grant awarded by National Science Foundation. The government has certain rights in the invention.

BACKGROUND

Hydrogels can be effective materials for a wide variety of applications. As one example, stimulus-responsive hydrogels can allow for high levels of control over material properties in response to external stimuli. For example, stimulus-responsive hydrogels can be formed using smart polymers, which can be tailored to respond to a variety of changes in environmental conditions, such as solvent composition, temperature, pH, light, etc. The response of the stimulus-responsive hydrogel to an environmental stimulus can be in the form of a change in refractive index, change in elastic modulus, change in color, etc. As such, stimulus-responsive hydrogels have been effective in advancing healthcare, improving tissue engineering and wound healing, and a variety of additional applications.

SUMMARY

Hydrogel sensor devices can include a crosslinked hydrogel body which changes in volume in response to an environmental stimulus, a support post positioned to mechanically support the crosslinked hydrogel body during the change in volume, and a sensor positioned to detect the change in volume of the crosslinked hydrogel body.

Methods of manufacturing a hydrogel sensor device can include preparing a crosslinked hydrogel body configured to change in volume in response to an environmental stimulus, positioning the crosslinked hydrogel network adjacent to a support post configured to mechanically support the crosslinked hydrogel body during the change in volume, and positioning a sensor to detect the change in volume of the crosslinked hydrogel body.

Methods of detecting an environmental stimulus can include preparing a crosslinked hydrogel body configured to change in volume in response to an environmental stimulus, positioning the crosslinked hydrogel network adjacent to a support post configured to mechanically support the crosslinked hydrogel body during the change in volume, and detecting the change in volume using a sensor.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a crosslinked hydrogel body" includes reference to one or more of such materials and reference to "detecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Hydrogel Sensor Assembly

The volumetric response (both response-time and magnitude) of a stimuli-responsive hydrogel is proportional to the initial volume of the hydrogel. This is because the volume response of a hydrogel is diffusion limited. Thus, the smaller the initial volume of the hydrogel, the faster it reaches the final changed volume, which leads to shorter response-times. Similarly, the larger the initial volume, the slower the hydrogel reaches its final changed volume, which leads to longer response-times. Generally, fast responses in seconds or minutes are desired for many sensor applications, whereas response times in hours are generally not useful in most applications. Therefore, use of smaller initial volumes for sensing applications is often desirable. However, standard geometries of smaller volumes of hydrogels are either not mechanically stable or have small response magnitudes, i.e. smaller changes in volume.

The present disclosure describes hydrogel sensor devices including crosslinked hydrogel bodies with (a) good mechanical stability, (b) fast response times, and (c) high response magnitudes. More specifically, the hydrogel sensor devices described herein can include a crosslinked hydrogel body which changes in volume in response to an environmental stimulus, a support post positioned to mechanically support the crosslinked hydrogel body during the change in volume, and a sensor positioned to detect the change in volume of the crosslinked hydrogel body.

It is also noted that when discussing the hydrogel sensor devices and methods described herein, each of these discussions can be considered applicable to the other examples, whether or not they are explicitly discussed in the context of that example. Thus, for example, in discussing, a crosslinked hydrogel body related to a hydrogel sensor device, such disclosure is also relevant to and directly supported in the context of the methods described herein, and vice versa.

Figure 1A:
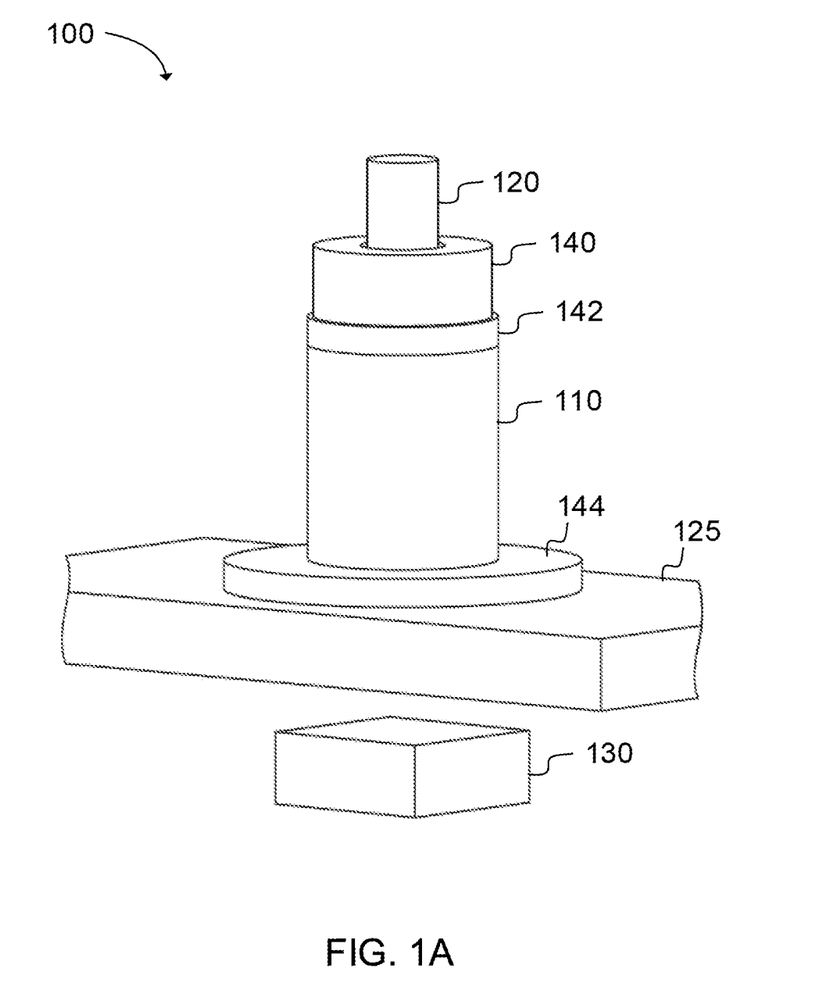
FIG. 1A depicts a perspective view of a hydrogel sensor device, in accordance with an example of the present disclosure.
Figure 1B:
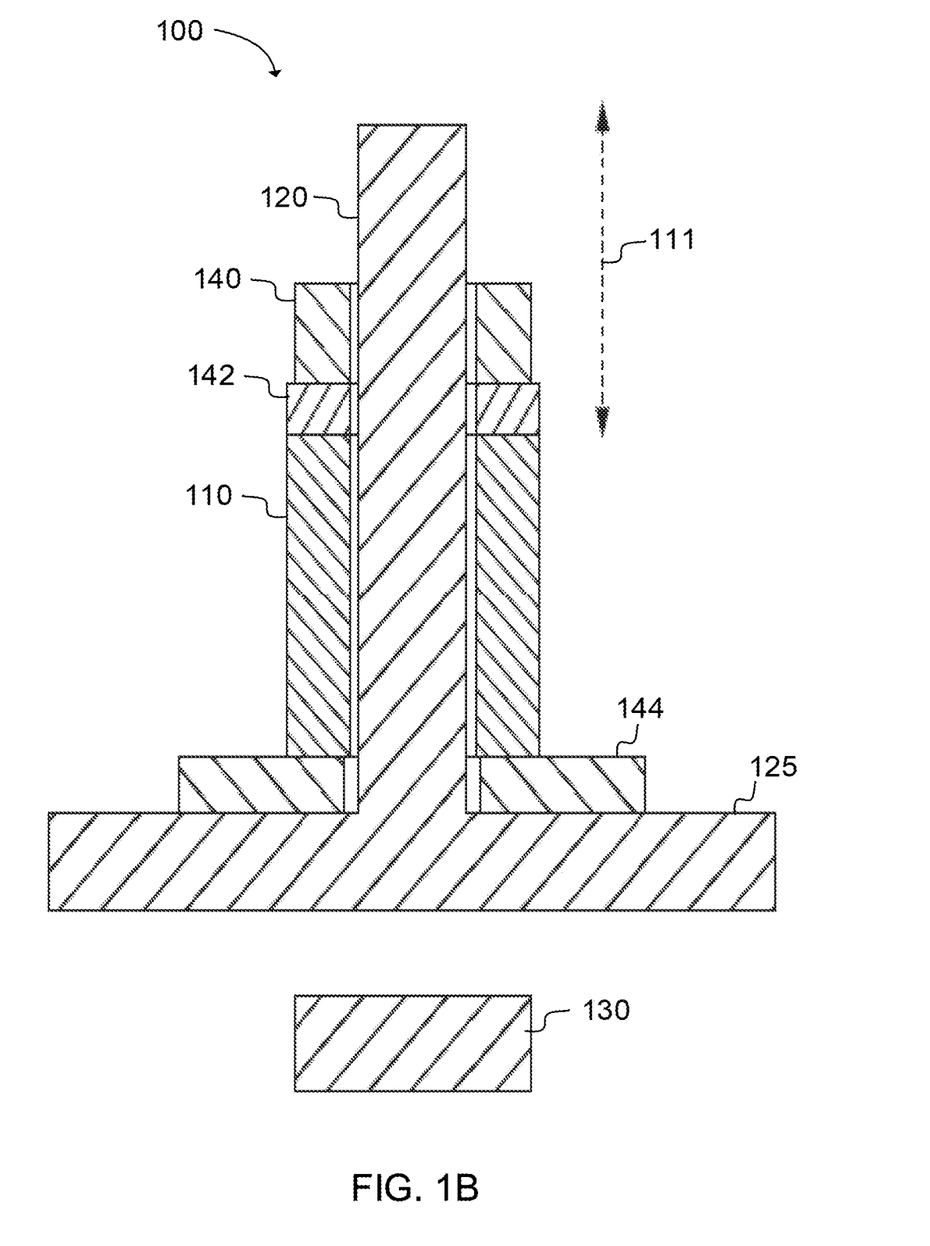
FIG. 1B depicts a cross-sectional view of the hydrogel sensor device of FIG. 1A.

FIGS. 1A and 1B illustrate one example of a hydrogel sensor device 100 which includes a crosslinked hydrogel body 110 mechanically supported by a support post 120. In this particular example, the support post 120 is circumscribed by the crosslinked hydrogel body 110. In other words, the crosslinked hydrogel body 110 can be a hollow body, such as a hollow annular cylinder in this example. In some examples, a hollow crosslinked hydrogel body can decrease the response time of the sensor device 100 because the inner portion of the crosslinked hydrogel body 110, which normally increases the response time due to longer diffusion lengths from the exposed surface, is replaced by the support post 120. As illustrated in FIGS. 1A-1B, the support post 120 can be attached to or integrally formed with a support base 125. A sensor 130 (a magnetometer, in this particular example) can be positioned adjacent the support base 125 at an opposite side of the support base 125 as the support post 120. A magnet 140 is positioned on the crosslinked hydrogel body 110. In some specific examples, a magnet-interface layer 142 can be positioned between the magnet 140 and the crosslinked hydrogel body 110. Further, in some additional examples, a base-interface layer 144 can be positioned between the support base 125 and the crosslinked hydrogel body 110. Thus, as the crosslinked hydrogel body 110 changes in volume in the direction of line 111, the distance between magnet 140 and the magnetometer 130 can change and the corresponding change in the magnetic field therebetween can be detected.

Figure 2:
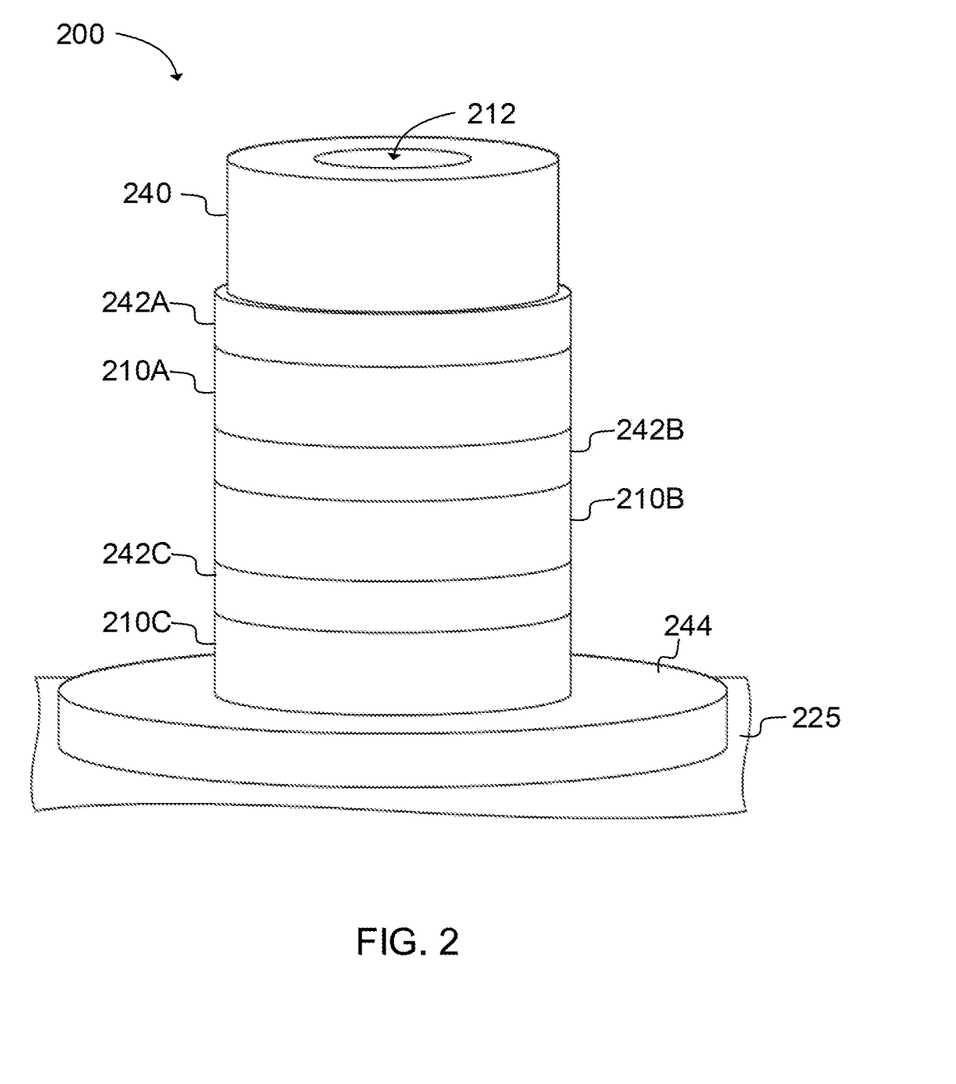
FIG. 2 depicts a perspective view of a hydrogel sensor device having multiple hydrogel bodies, in accordance with an example of the present disclosure.

FIG. 2 illustrates an alternative example of a hydrogel sensor device 200 that includes a plurality of stacked crosslinked hydrogel bodies 210A, 210B, 210C. It is noted that while FIG. 2 specifically illustrates a device including three stacked crosslinked hydrogel bodies, this is not to be construed as limiting. Any suitable number of hydrogel bodies can be employed (e.g. 2, 3, 4, 5, etc.). In this particular example, crosslinked hydrogel body 210A is positioned between magnet-interface layer 242A and hydrogel-interface layer 242B, crosslinked hydrogel body 210B is positioned between hydrogel-interface layers 242B and 242C, and crosslinked hydrogel body 210C is positioned between hydrogel-interface layer 242C and base-interface layer 244. The base-interface layer 244 further interfaces with the support base 225. It is further noted that this particular illustration does not show the support post (e.g. support post 120 from FIGS. 1A-1B) in order to more clearly illustrate the hollow portion or hollow channel 212 formed through the center of the stack. Further, the magnet 240 is similarly illustrated as an annular body that can be slidably engaged over a support post concentrically positioned within hollow channel 212. It is noted that, in this example, each of the magnet 240, the crosslinked hydrogel bodies 210A, 210B, 210C, and hydrogel-interfacing layers 242A, 242B, 242C, 244 are annular bodies. The stacked hydrogel configuration can be advantageous in cases such as to adjust the sensing range and sensitivity of the hydrogel sensor device. Typically, hydrogel crosslinked polymers exhibit high sensitivity in a narrow sensing range and the sensitivity drops dramatically outside of this narrow sensing range, in order to extend the sensing range while retaining the high sensitivity, different hydrogel crosslinked polymers may be formulated for different ranges of sensitivity and stacked as described in this example. This configuration can also provide a better mechanical integrity. Depending on the chemistry and formulation of the hydrogel, the rheological properties of the hydrogel vary. Having a stacked configuration provides improved mechanical stability of the hydrogels that tend to deform with their own weight. Furthermore, this configuration allows integration of different hydrogels detecting different species. This can be advantageous to tailor the specificity as needed by the application.

In further detail, a variety of hydrogel materials can be used to form the crosslinked hydrogel body. In some specific examples, the crosslinked hydrogel body can be formed using a primer backbone monomer or repeat unit and a crosslinking monomer or repeat unit. Non-limiting examples of primary monomers can include 2-hydroxyethyl methacrylate (HEMA), 2-hydroxypropyl methacrylate (HPMA), acrylamide (AAm), acrylic acid (AAc), N-isopropylacrylamide (NIPAm), polyethylene glycol monoacrylate (PEGMA), methoxyl polyethylene glycol monoacrylate (mPEGMA), the like, or a combination thereof. In some specific examples, the primary monomer or repeat unit can include AAm, an N-substituted AAm, or a combination thereof. In some examples, the crosslinked hydrogel body can be formed of a hydrophilic polymer.

The primary monomer or repeat unit can generally be present in the crosslinked hydrogel body in an amount greater than 70 mol %, or greater than 80 mol %. In some specific examples, the primary monomer or repeat unit can be present in the crosslinked hydrogel body in an amount of from about 89 mol % to about 99.99 mol %, and in some cases 80 mol % to 95 mol %, and in other cases from 85 mol % to about 94 mol %.

A variety of suitable crosslinking agents or crosslinking monomers can also be incorporated into the crosslinked hydrogel body. Generally, any suitable crosslinking agent or crosslinking monomer that is suitable to covalently crosslink individual polymer chains of the hydrogel bodies described herein can be employed. Non-limiting examples can include N,N'-methylenebis(acrylamide) (MBAA), N,N-diallylacrylamide, ethylene glycol diacrylate (EGDA), polyethylene glycol diacrylate (PEGDA), polyethylene glycol dimethacrylate (PEGDMA), and combinations thereof. In some specific examples, the crosslinking monomer can be or include MBAA.

The crosslinking monomer can be present in the crosslinked hydrogel body in a sufficient amount to maximize the detectable volume change of the hydrogel, but without loss of structural integrity that can lead to polymer chain segregation. In some specific examples, the crosslinking monomer can be present in the crosslinked polymer body in an amount of from about 0.01 mol % to about 10 mol %, and in some cases from 0.25 mol % up to about 5 mol %.

The crosslinked hydrogel body can be configured to change in volume in response to a variety of environmental stimuli, such as presence or absence of a target molecule, temperature, pH, light, ultrasonic radiation, magnetic field, electric field, ionic strength, etc. In some specific examples, the crosslinked hydrogel body can be configured to change in volume in response to the presence or absence of a particular target molecule. Non-limiting examples of such crosslinked hydrogels are described in U.S. patent application Ser. No. 16/176,813, filed Oct. 31, 2018, which is incorporated herein by reference in its entirety. In other examples, the crosslinked hydrogel body can be configured to change in volume in response to pH. In additional examples, the crosslinked hydrogel body can be configured to change in volume in response to temperature. In still other examples, the crosslinked hydrogel body can be configured to change in volume in response to ionic strength. In other examples, the crosslinked hydrogel body can be configured to change in volume in response to specific sugars such as glucose, lactose, fructose, etc. In other examples, the crosslinked hydrogel body can be configured to change in volume in response to lactate. In other examples, the crosslinked hydrogel body can be configured to change in volume in response to light. In further examples, the crosslinked hydrogel body can be configured to change in volume in response to ultrasonic radiation, magnetic field, electric field, or the like. Non-limiting examples of specific hydrogels that are configured to change in volume in response to various environmental stimuli are discussed in *pH Sensitive Hydrogels in Drug Delivery: Brief History, Properties, Swelling, and Release Mechanism, Material Selection and Applications*. Muhammad Rizwan et al., Polymers 2017, 9(4), p. 137, *Hydrogel-Based Glucose Sensors: Effects of Phenylboronic Acid Chemical Structure on Response*, Zhang et al., Chemistry of Materials 2013, 25 (15), pp 3239-3250, which are each incorporated herein by reference are examples of suitable hydrogels and corresponding volumetric responses.

Figure 3A:
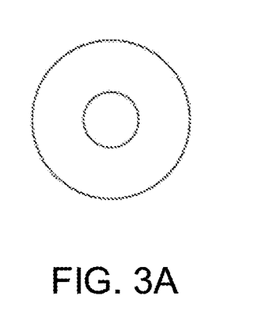
FIGS. 3A-3I depict various cross-sectional geometries of a hydrogel body, in accordance with examples of the present disclosure.
Figure 3B:
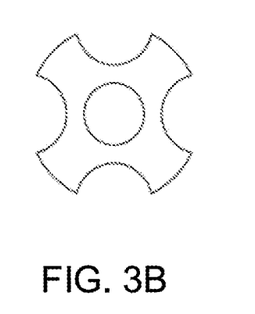
Figure 3C:
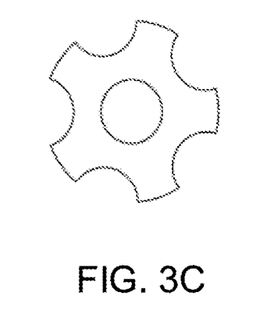
Figure 3D:
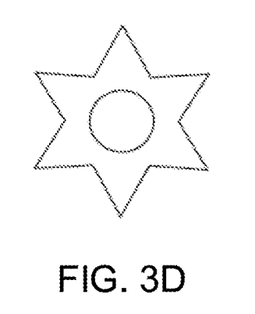
Figure 3E:
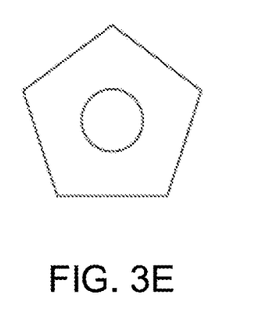
Figure 3F:
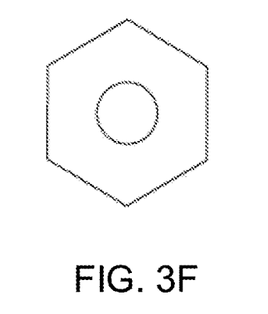
Figure 3G:
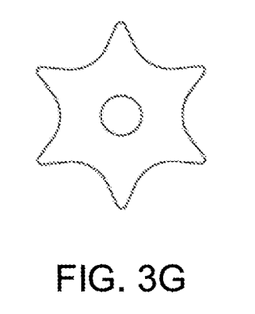
Figure 3H:
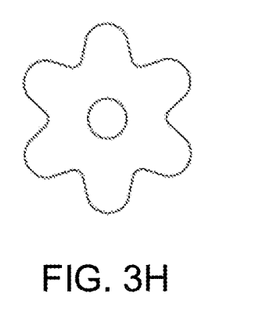
Figure 3I:
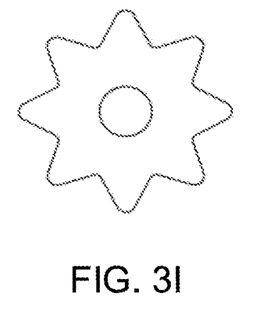

Generally, the lower the ratio of the exposed surface area of the hydrogel body to the volume of the hydrogel body (S/V), the slower the response time will be. As described above, slow response times are typically not very useful for sensor applications. As such, the crosslinked hydrogel bodies disclosed herein can typically have a relatively high S/V. In some specific examples, the crosslinked hydrogel body can have an S/V of at least 3.0 $mm^{-1}$. In other examples, the crosslinked hydrogel body can have an S/V of at least 3.5 $mm^{-1}$, at least 4.0 $mm^{-1}$, at least 4.5 $mm^{-1}$, at least 5.0 $mm^{-1}$, or at least 5.5 $mm^{-1}$. FIGS. 3A-3I illustrate a number of potential crosslinked hydrogel body geometries. For example, FIG. 3A illustrates a crosslinked hydrogel body geometry having an S/V of about 3.02 $mm^{-1}$, FIG. 3B illustrates a crosslinked hydrogel body geometry having an S/V of about 5.00 $mm^{-1}$, FIG. 3C illustrates a crosslinked hydrogel body geometry having an S/V of about 5.03 $mm^{-1}$, FIG. 3D illustrates a crosslinked hydrogel body geometry having an S/V of about 5.94 $mm^{-1}$, and FIG. 3E illustrates a crosslinked hydrogel body geometry having an S/V of about 3.23 $mm^{-1}$. Thus, each of the geometries illustrated in FIGS. 3A-3E has an S/V of at least 3.0 $mm^{-1}$. In contrast, FIGS. 3F-3I illustrate geometries having an S/V lower than 3.0 $mm^{-1}$. Specifically, FIG. 3F illustrates a crosslinked hydrogel body geometry having an S/V of about 2.97 $mm^{-1}$, FIG. 3G illustrates a crosslinked hydrogel body geometry having an S/V of about 2.815 mm$^{-1}$, FIG. 3H illustrates a crosslinked hydrogel body geometry having an S/V of about 2.4 mm$^{-1}$, and FIG. 3I illustrates a crosslinked hydrogel body geometry having an S/V of about 2.89 mm$^{-1}$.

Thus, the crosslinked hydrogel body can be shaped to have a geometry that achieves a minimum S/V, such as at least at least 2.4 mm$^{-1}$, in some cases at least 2.6 mm$^{-1}$, and often at least 3.0 mm$^{-1}$, for example. It is further noted that the general geometry of the hydrogel can be self-sustaining, rather than maintained by the walls of a container, or the like. Thus, with the exception of lower and upper surfaces of the crosslinked hydrogel body, in some examples, the crosslinked hydrogel body can generally be unbounded, or substantially unbounded. By "unbounded" or "substantially unbounded," it is meant that the general shape or geometry (taking into account geometrical changes associated with changes in volume due to swelling/de-swelling of the hydrogel body) of the crosslinked hydrogel body is self-sustaining and that the crosslinked hydrogel body is substantially mechanically unsupported other than by a lower support surface (e.g. support base 125, support arm 722, for example) and one or more support posts.

Generally, the crosslinked hydrogel body, or crosslinked hydrogel body stack (e.g. stack illustrated in FIG. 2, for example) can have a height (e.g. in the direction of line 111 or arrow 711, for respective orientations of the crosslinked hydrogel body) that is shorter than the support post, whether in a swollen or non-swollen state. In some specific examples, the height of the crosslinked hydrogel body, or crosslinked hydrogel body stack, can be from about 0.1 mm to about 5 mm in a non-swollen state. In still other examples, the crosslinked hydrogel body, or crosslinked hydrogel body stack, can have a height of from about 0.5 mm to about 4 mm in a non-swollen state. In some examples, the heights disclosed for the crosslinked hydrogel body, or crosslinked hydrogel body stack, can include interfacing layers, such as hydrogel-interfacing layers, a base interfacing layer, and a magnet-interfacing layer, for example.

As disclosed above, in some examples, the crosslinked hydrogel body can be a hollow crosslinked hydrogel body. Where this is the case, the diameter of the hollow portion or hollow channel through the crosslinked hydrogel body can generally be larger (when the hydrogel is in a non-swollen state) than a diameter of a support post positioned within the hollow channel, when present. For example, the diameter of the hollow channel can generally be large enough to accommodate the volume change of the crosslinked hydrogel body during its swelling response without being overly restricted by the support post. In some specific examples, the diameter of the hollow channel can be from about 0.5 mm to about 3 mm when the crosslinked hydrogel body is in a non-swollen state. In other examples, the diameter of the hollow channel can be from about 0.7 mm to about 2 mm when the crosslinked hydrogel body is in a non-swollen state.

Turning again to FIG. 2, the hydrogel sensor device 200 is illustrated with various hydrogel-interfacing layers, such as magnet-interfacing layer 242A, base-interfacing layer 244, and additional hydrogel-interfacing layers 242B, 242C. It is noted that various hydrogel-interfacing layers can be employed, depending on the particular application of the hydrogel sensor device. In some examples, the hydrogel-interfacing layers can help prevent or minimize delamination between adjacent layers or components. In some additional examples, the various hydrogel-interfacing layers can impart greater structural integrity to the crosslinked hydrogel body or crosslinked hydrogel body stack. In some specific examples, the hydrogel sensor device can include a base-interfacing layer (e.g. 244) alone or in combination with additional interfacing layers. In some specific examples, the base-interfacing layer can include a polymer, or combination of polymers, to bond the base-interfacing layer to both the support base and the crosslinked hydrogel body. In some other specific examples, the hydrogel sensor device can include a magnet-interfacing layer (e.g. 242A) alone or in combination with additional interfacing layers. In some specific examples, the magnet-interfacing layer can include a polymer, or combination of polymers, to bond the magnet-interfacing layer to both a magnetic material (e.g. a magnet) and the crosslinked hydrogel body. In some examples, the hydrogel sensor device can include both a base-interfacing layer and a magnet-interfacing layer. In some other examples, the hydrogel sensor device does not include a hydrogel-interfacing layer (e.g. a base-interfacing layer, a magnet-interfacing layer, etc.).

In some cases, the hydrogel layer or an intervening interface layer can be oriented in contact with the support base. Although the contact may be merely mechanical contact, in some cases the contact interface can include a bonding mechanism (i.e. functional chemical bonding, adhesive, etc) which prevents the hydrogel from sliding off of the support post. Alternatively, or in addition, the support post can include a stop at a distal end having a dimension greater than an inner dimension of the hydrogel. Such a stop can include a bulbous tip, cross beam, flared tip, etc.

The various interface layers can have a variety of heights (e.g. in the direction of line 111 or arrow 711, for respective orientations of the crosslinked hydrogel body). In some specific examples, the various interface layers can have a height of from about 0.05 mm to about 1 mm. In other examples, the various interface layers can have a height of from about 0.1 mm to about 0.8 mm. It is further noted, that where more than one interface layer is employed, the plurality of interface layers can have the same height, can have different heights, or a combination thereof.

The various interface layers can be made of a variety of materials. Non-limiting examples can include polyester, polycarbonate, high density polyethylene (HDPE), polypropylene, polyether ether ketone (PEEK), the like, or a combination thereof. In some further examples, an interfacing surface (i.e. a surface interfacing with another layer or component) of a hydrogel-interfacing layer can be activated to form chemical or physical bonds with the hydrogel, the magnet, the support base, or other surface with which the hydrogel-interfacing layer interfaces. In some examples, chemical activation of the interfacing surface can form a monolayer of active molecules that can form covalent bonds with the hydrogel during hydrogel polymerization. For example, the bound monolayer on the polymer film can include acrylates, acrylamides, the like, or a combination thereof so that these molecules can form covalent bonds with acrylamide-based hydrogels, or the like, during any radical polymerization. Physical activation of the interfacing surface can include plasma activation or roughening of the interfacing surface using processes such as sand-blasting, or the like. In some examples, surface activation can be achieved via a combination of chemical and/or physical activation processes. Regardless, the interface layer can provide mechanical bonding with the magnet, support base or other adjacent materials, as well as decrease delamination concerns by providing an intermediate stiffness material.

Figure 4:
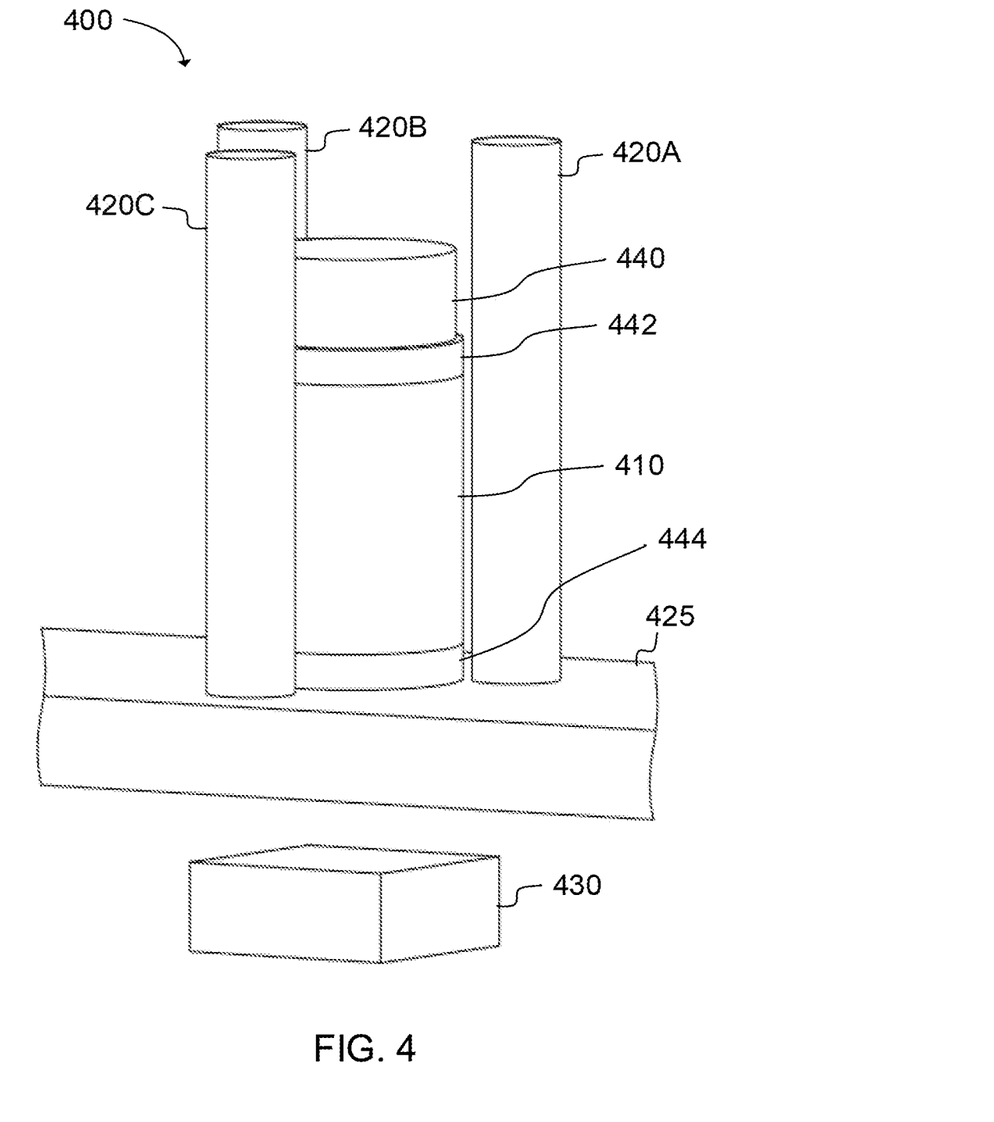
FIG. 4 depicts a perspective view of a hydrogel sensor device having multiple peripheral posts, in accordance with an example of the present disclosure.

Returning again to FIGS. 1A-1B, the hydrogel sensor device 100 is illustrated with a support post 120 concentrically disposed interior to the crosslinked hydrogel body 110. As described above, this can be an effective arrangement between the crosslinked hydrogel body 110 and the support post 120 because the support post 120 replaces a central portion of the crosslinked hydrogel body that is typically associated with increased response times due to longer diffusion lengths from the exposed surface of the crosslinked hydrogel body 110. However, as illustrated in FIG. 4, this arrangement is not required. More specifically, hydrogel sensor device 400 has a configuration where the crosslinked hydrogel body 410 is mechanically supported by a plurality of support posts 420A, 420B, 420C positioned about a lateral perimeter of the crosslinked hydrogel body 410. Otherwise, the hydrogel sensor device 400 is similar to the hydrogel sensor device 100 illustrated in FIGS. 1A-1B. For example, hydrogel sensor device 400 includes a base-interfacing layer 444 disposed between the crosslinked hydrogel body 410 and a support base 425. Further, the hydrogel sensor device 400 includes a magnet-interfacing layer 442 disposed between the crosslinked hydrogel body 410 and a magnet 440. A sensor 430 (in this case a magnetometer) is positioned adjacent the support base 425 at a side of the support base 425 opposite the plurality of support posts 420A, 420B, 420C.

Figure 5:
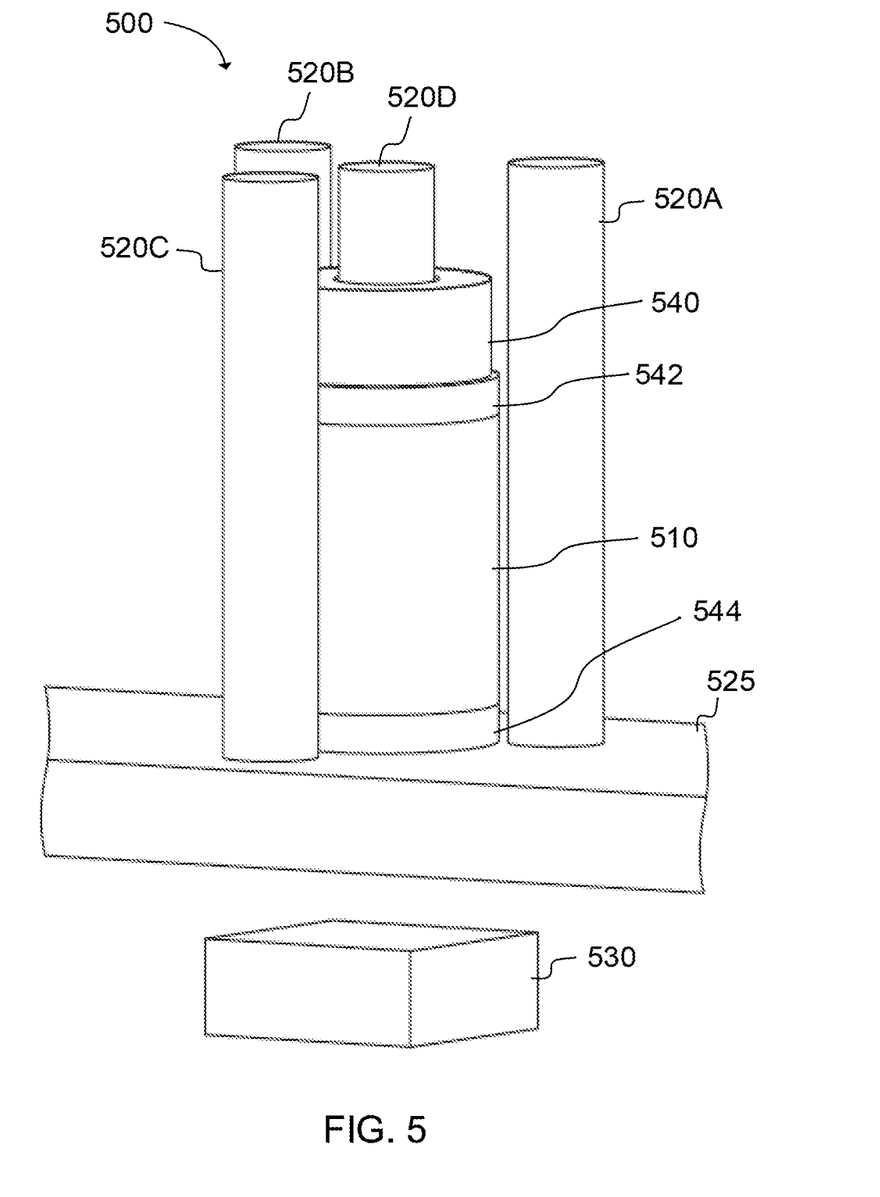
FIG. 5 depicts a perspective view of another hydrogel sensor device having multiple posts, in accordance with an example of the present disclosure.

FIG. 5 illustrates a similar embodiment of a hydrogel sensor device 500 including a plurality of support posts 520A, 520B, 520C positioned about a lateral perimeter of the crosslinked hydrogel body 510. However, in this particular example, the crosslinked hydrogel body 510 is also hollow and a post 520D is concentrically positioned within the hollow channel defined by the crosslinked hydrogel body 510 to provide additional mechanical support. Otherwise, the hydrogel sensor device 500 is similar to hydrogel sensor device 400 as illustrated in FIG. 4. For example, hydrogel sensor device 500 includes a base-interfacing layer 544 disposed between the crosslinked hydrogel body 510 and a support base 525. Further, the hydrogel sensor device 500 includes a magnet-interfacing layer 542 disposed between the crosslinked hydrogel body 510 and a magnet 540. A sensor 530 (in this case a magnetometer) is positioned adjacent the support base 525 at a side of the support base 525 opposite the plurality of support posts 520A, 520B, 520C, 520D.

It is noted that where a support post is included about or along a lateral perimeter of the crosslinked hydrogel body, typically a plurality of support posts can be positioned about the lateral perimeter. In some examples, where a centrally positioned support post is employed (e.g. as in FIGS. 1A-1B, or FIG. 5, for example) a plurality of perimeter support posts may not be needed. However, in some examples, a plurality of peripherally positioned support posts can be positioned along the lateral perimeter of the crosslinked hydrogel body and spaced apart from one another to provide mechanical support to the crosslinked hydrogel body and in some cases to provide mechanical protection to the hydrogel against damage from impact of debris or objects. It is noted that the support posts can generally be placed at a sufficient distance from the crosslinked hydrogel body to allow a free swelling response of the crosslinked hydrogel body. Further, the dimensions of the support posts and number of support posts around the crosslinked hydrogel body can be configured to not adversely affect (or restrict) the interaction of crosslinked hydrogel body with the environmental stimulus effectuating the change in volume (e.g. maximizing or increasing exposed surface area to volume ratios). As such, the support post generally does not form a contiguous wall circumscribing the crosslinked hydrogel body.

In some specific examples, the spacing between each (or at least 2) peripherally positioned support posts can be less than 180 degrees. In other examples, the spacing between each (or at least 2) peripherally positioned support posts can be less than 150 degrees, or 120 degrees. In some examples, the spacing between adjacent peripherally positioned support posts can be equidistant, the spacing between adjacent peripherally positioned support posts can be non-equidistant, or a combination thereof. In some specific examples, the hydrogel sensor device includes at least 3 peripherally positioned support posts. In some additional examples, the hydrogel sensor device includes at least 4, at least 5, or at least 6 peripherally positioned support posts. In some examples, the hydrogel sensor device does not include any peripherally positioned support posts.

The support posts can have a variety of shapes or geometries. In some examples, the support post can have a circular geometry, forming a cylindrically shaped post. In other examples, the support post can have other suitable geometries, such as ovular, triangular, square, polygonal, other suitable geometries, or a combination thereof. In some examples, the geometry of the support post can be configured to match a hollow channel through the crosslinked hydrogel body, or other geometric feature of the crosslinked hydrogel body, which can also include the geometries disclosed herein.

Turning again to FIGS. 1A-1B, the support post 120 can typically be connected to a support base 125. In some examples, the support post 120 can be integrally formed with the support base 125 so that the support post 120 and the support base are part of a single monolithic structure. In other examples, the support post 120 can be subsequently or separately connected to the support base 125, such with adhesives, fasteners (e.g. screws, pins, etc.), welds, threaded fittings, interference fitting, the like, or a combination thereof.

As previously discussed, the support post can typically have a height (i.e. in the direction of line 111 or arrow 711, for respective orientations of the support post) that is greater than a height of the crosslinked hydrogel body or crosslinked hydrogel body stack. In some specific examples, the support post can have a height of from about 1 mm to about 10 mm. In other examples, the support post can have a height of from about 2 mm to about 8 mm.

Additionally, the support post can typically have a diameter that is sufficient to provide mechanical support to the crosslinked hydrogel body, but that does not significantly interfere with the volume-changing response of the crosslinked hydrogel body. Thus, depending on the positioning of the support post (e.g. peripherally positioned vs. concentrically positioned), the support posts can have different diameters. In some specific examples, the support post can have a diameter of from about 0.5 mm to about 2 mm. In other examples, the support post can have a diameter of from about 0.8 mm to about 1.5 mm. In some examples, the support post can be tapered such that the diameter changes along a height thereof. In general, a gap between the hydrogel inner surface and the post outer surface can be sufficient to allow expansion to full contact upon a maximum swelling volume. In some examples, this gap can be from about 0.05 mm to about 5 mm.

The support post and support base can be made of a variety of materials. In some examples, the support post and the support base can be made of a non-magnetic material (e.g. a non-ferrous metal or non-ferromagnetic material, for example). In some specific examples, the support post and the support base can be made of a polymeric material.

Non-limiting examples can include poly-carbonate, liquid-crystal polymers, polystyrene, high-density polyethylene (HDPE), polypropylene, the like, or a combination thereof. In some examples, the support post and the support base can include or be made of the same material(s). In other examples, the support post and the support base can include or be made of different materials. In some additional examples, the support post can be made of a hydrophobic material or other suitable material (e.g. glass, quartz, etc.) to minimize interactions between the crosslinked hydrogel body and the support post. In other examples, the support post can be coated with or lubricated with a hydrophobic material to minimize mechanical friction or sticking interactions between the crosslinked hydrogel body and the support post. It is further noted that, in some examples, the support post can be rigid (i.e. substantially inflexible or minimally flexible so as to not flex during operation).

The hydrogel sensor devices disclosed herein can include a variety of sensors. For the sake of brevity and clarity, particular emphasis is placed on magnetometers in this disclosure. However, this is not to be construed as limiting. Additional examples of detectors can include ultrasonic sensors, electrical inductors, pressure sensors or mechanical transducers, optical sensors, other suitable sensors, or combinations of suitable sensors. Non-limiting examples of pressure sensors can include piezoresistive strain gauges, capacitive pressure detectors, electromagnetic pressure sensors, piezoelectric pressure sensors, strain gauges, potentiometric pressure detectors, the like, or a combination thereof. Additionally, a variety of optical measurements can be employed to detect changes in volume in the crosslinked hydrogel body. For example, the optical detector can represent an interferometric detector or other suitable optical distance detector and a mirror (e.g. in the place of the magnet 140 in FIG. 1A) or other suitable surface can be employed to reflect a beam of coherent light back to the optical detector to measure a change in distance between the mirror and the optical detector. Other suitable optical measurements can also be employed, such as refractive index measurements, luminescence detection, etc. Additional details can be found in U.S. patent application Ser. No. 16/176,813, filed Oct. 31, 2018, and U.S. patent application Ser. No. 15/006,172, filed Jan. 26, 2016, each of which is incorporated herein by reference.

Corresponding detectors can produce data in the form of a detector response signal (e.g. voltage change, fluorescence signal, intensity, magnetic field value, etc.) which can be collected by a memory device. The memory device can store such data for later analysis or simultaneously communicate collected data to a computing device. For example, a computing device on which collection, correlation, analysis, and/or output of this technology can be used. In one example, collected data can be compared to a reference dataset. The reference dataset can be produced through subjecting the detectors to known environment stimuli (e.g. concentrations of target molecules, for example) to obtain data of detector response as a function of the environmental stimuli. In this manner, collected data can be compared with the reference dataset to determine a corresponding response in an unknown fluid.

The computing device may include one or more processors that are in communication with memory devices. The computing device may include a local communication interface for the components in the computing device. For example, the local communication interface may be a local data bus and/or any related address or control busses as may be desired.

The memory device may contain modules that are executable by the processor(s) and data for the modules. The modules may execute functions that perform the methods described herein. A data store may also be located in the memory device for storing data related to the modules and other applications along with an operating system that is executable by the processor(s).

The computing device may also have access to I/O (input/output) devices that are usable by the computing devices. An example of an I/O device is a display screen that is available to display output from the computing device. Networking devices and similar communication devices may be included in the computing device. The networking devices may be wired or wireless networking devices that connect to the internet, a LAN, WAN, or other computing network.

The components or modules that are shown as being stored in the memory device may be executed by the processor(s). The term "executable" may mean a program file that is in a form that may be executed by a processor. For example, a program in a higher level language may be compiled into machine code in a format that may be loaded into a random access portion of the memory device and executed by the processor, or source code may be loaded by another executable program and interpreted to generate instructions in a random access portion of the memory to be executed by a processor. The executable program may be stored in any portion or component of the memory device. For example, the memory device may be random access memory (RAM), read only memory (ROM), flash memory, a solid state drive, memory card, a hard drive, optical disk, floppy disk, magnetic tape, or any other memory components.

The processor may represent multiple processors and the memory device may represent multiple memory units that operate in parallel to the processing circuits. This may provide parallel processing channels for the processes and data in the system. The local interface may be used as a network to facilitate communication between any of the multiple processors and multiple memories. The local interface may use additional systems designed for coordinating communication such as load balancing, bulk data transfer and similar systems.

The detector response data may also be stored on a computer readable storage medium that includes volatile and non-volatile, removable and non-removable media implemented with any technology for the storage of information such as computer readable instructions, data structures, program modules, or other data.

The devices described herein may also contain communication connections or networking apparatus and networking connections that allow the devices to communicate with other devices. By way of example and not limitation, communication media includes wired media such as a wired network or direct-wired connection and wireless media such as acoustic, radio frequency, infrared and other wireless media. The term computer readable media as used herein includes communication media.

Turning again to FIGS. 1A-1B, the hydrogel sensor device 100 can include a magnetometer 130. The magnetometer 130 can be positioned in proximity to a magnet 140 or other magnetic material to detect changes in magnetic field between the magnetometer 130 and the magnet 140. In this particular example, the magnetometer 130 is positioned adjacent to the support surface 125 on a side opposite the magnet 140. As the crosslinked hydrogel body changes in volume in the directions of line 111, the distance between the magnetometer 130 and the magnet 140 will change and the corresponding change in magnetic field can be detected. Thus, in this example, the magnet 140 can move substantially perpendicular to the plane, or an upper surface, of the magnetometer 130.

Figure 6:
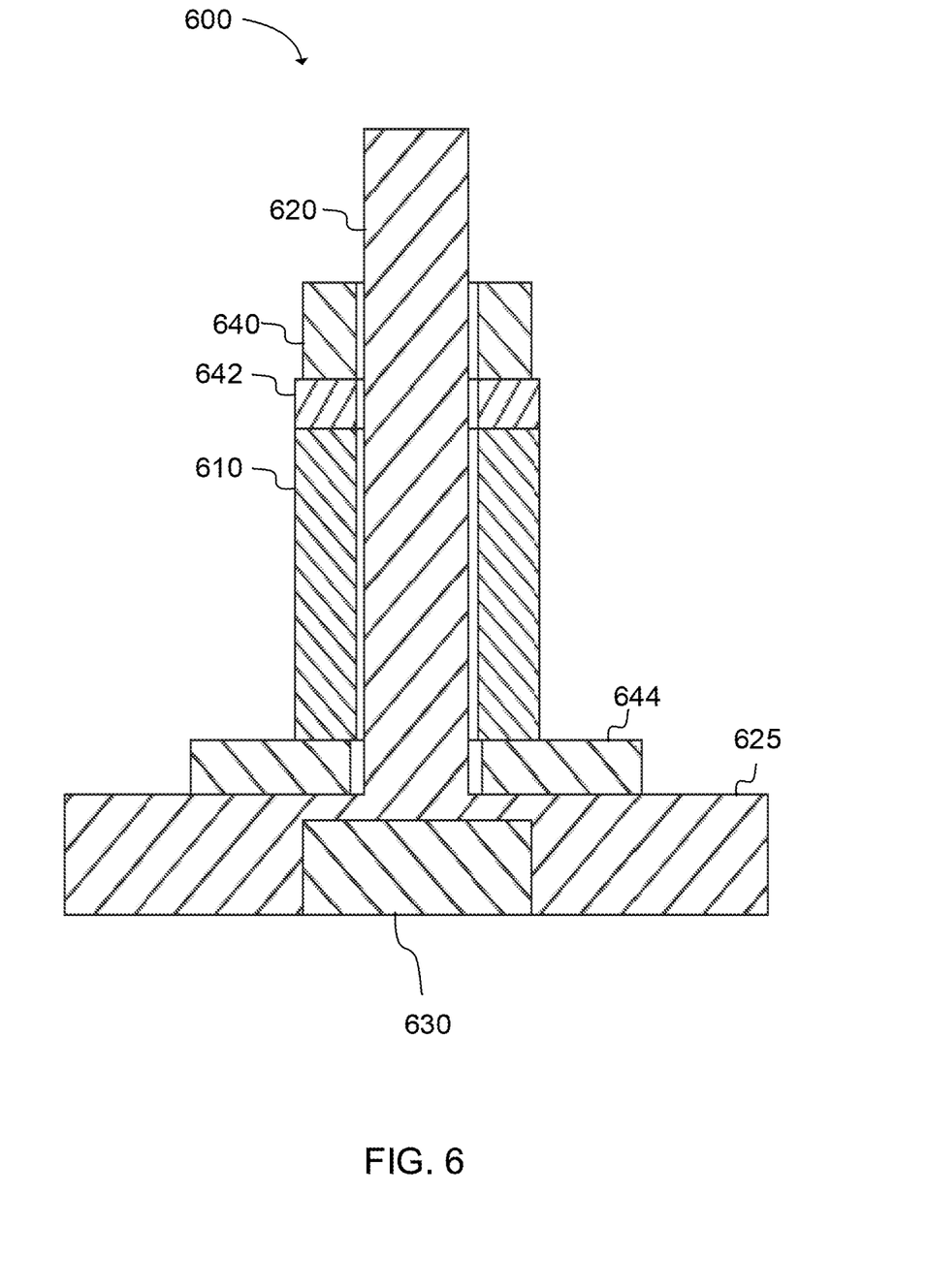
FIG. 6 depicts a cross-sectional view of another example of a hydrogel sensor device having a magnetometer embedded in a support base, in accordance with an example of the present disclosure.

FIG. 6 illustrates a similar example of a hydrogel sensor device 600 where the magnetometer 630 is incorporated into the support base 625. More specifically, in this example, the magnetometer 630 is situated within the support base 625 (e.g. part of a chip, for example) at a position directly beneath the support post 620. Otherwise, the hydrogel sensor device 600 is similar to hydrogel sensor device 100 as illustrated in FIGS. 1A-1B. For example, a base-interfacing layer 644 is positioned between the crosslinked hydrogel body 610 and the support base 625. Additionally, a magnet-interfacing layer 642 is positioned between the crosslinked hydrogel body 610 and magnet 640.

Figure 7:
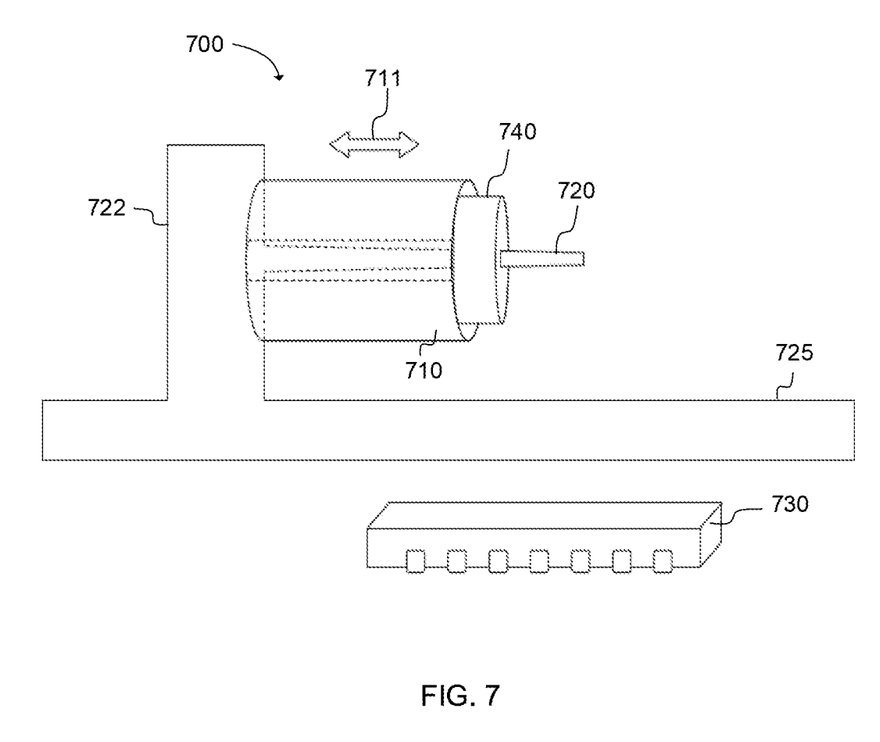
FIG. 7 depicts a partial perspective view of yet another example of a hydrogel sensor device in which a support post is oriented parallel to a plane of the magnetometer, in accordance with an example of the present disclosure.

Turning to FIG. 7, hydrogel sensor device 700 has a somewhat different configuration and orientation as compared to other hydrogel sensor devices disclosed previously. In this example, the magnetometer 730 is again positioned adjacent the support base 725 at a side opposite the support post 720 and magnet 740. However, the support post 720 is not directly connected to the support base 725 in this example. Rather, the support post 720 is indirectly connected to the support base 725 via support arm 722. Further, the support post 720 is oriented substantially parallel to the support base 725, rather than substantially perpendicular as in previous examples. Thus, in this particular example, the crosslinked hydrogel body 710 can change in volume in the directions of arrow 711. As such, in this example, the magnet 740 can move substantially parallel to a plane, or upper surface, of magnetometer 730. Thus, the position of the magnet 740 relative to the magnetometer 730 can change based on changes in volume of the crosslinked hydrogel body and the corresponding changes in magnetic field therebetween can be detected. It is also noted that the support post 720 in this example has a tapered structure, although this is not required.

Figure 8:
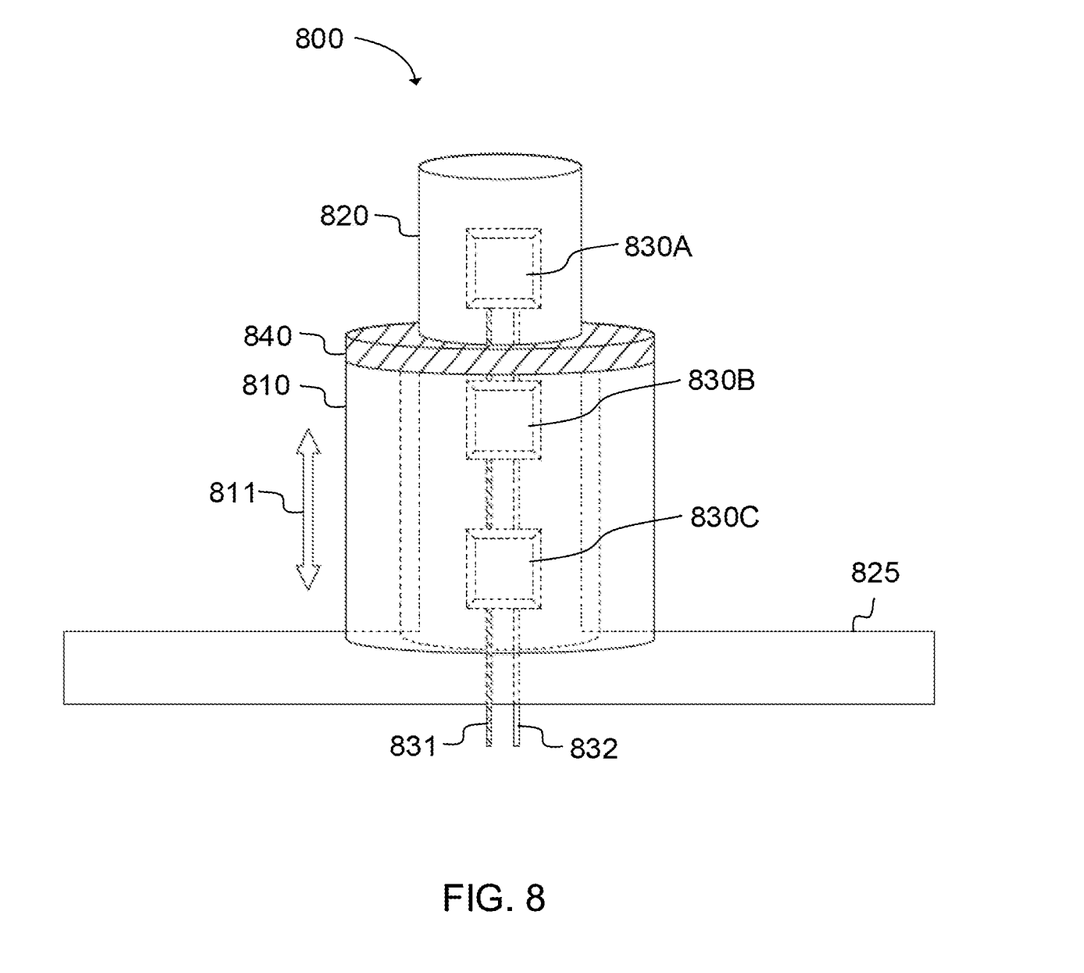
FIG. 8 depicts a partial perspective view of still another example of a hydrogel sensor device having magnetometer embedded within the support post, in accordance with an example of the present disclosure.

As illustrated in FIG. 8, a hydrogel sensor device 800 can include one or more magnetometers such as 830A, 830B, 830C embedded within the support post 820. As such, in this example, the magnetometers 830A, 830B, 830C are positioned on the same side of the support base 825 as the magnetic material 840. Further, in this particular example, the magnetic material 840 can represent a hydrogel-interfacing layer having magnetic particles embedded therein, as opposed to a single solid permanent magnet such as those shown in FIGS. 1A-2. Thus, as the crosslinked hydrogel body 810 changes in volume in directions of arrow 811, the position of the magnetic material 840 (i.e. hydrogel-interfacing layer having magnetic particles embedded therein) can change relative to magnetometers 830A, 830B, 830C and the corresponding change in magnetic field can be detected. In this particular example, individual magnetometers 830A, 830B, 830C can be connected along common electrical connections to positive 831 and negative 832 terminals or interconnects.

Thus, the magnetometer(s) can be positioned in a variety of locations relative to the magnet or other magnetic material to detect magnetic field changes due to changes in volume of the crosslinked hydrogel body. Additionally, in some examples, the magnetic material can be or include a single permanent magnet or a plurality of permanent magnets. In other examples, the magnetic material can include magnetic particles embedded within another component of the sensor device, such as a hydrogel-interfacing layer.

Where a single magnet or other magnetic material is used, the magnet or other magnetic material can typically be concentrically positioned relative to the crosslinked hydrogel body. In other examples, where a plurality of smaller magnets or magnetic particles are employed, they can typically be uniformly, or substantially uniformly, distributed on top of the crosslinked hydrogel body. In some specific examples, the magnetic material (e.g. a magnet, or a hydrogel-interfacing layer embedded with magnetic particles, for example) may be conformally coated for protection from corrosion using a metal, a ceramic, a polymer, or a combination thereof. In some examples, a thickness of the protective coating can be in the range of from about 0.1 micrometers to about 100 micrometers. Additionally, an epoxy, an adhesive, a direct bonding technique, or other technique of attaching the magnetic material to the crosslinked hydrogel body, or crosslinked hydrogel body stack, can be used.

Generally, the magnetic material can include a rare-earth metal, a ferromagnetic metal, the like, or a combination thereof. In some examples, other suitable magnetic materials can also be used alone or in combination with a rare-earth metal and/or a ferromagnetic metal. The magnetic field strength of the magnet or magnetic material on their surface can be from about zero (for ferromagnetic metals) to about 5000 Gauss. Thus, in some cases the magnetic material can be a permanent magnet.

The magnetic material can have a variety of suitable dimensions. In some examples, the magnetic material can have a height (i.e. in the directions of line 111 or arrow 711, depending on the respective orientation of the crosslinked hydrogel body) of from 0.1 mm to 2 mm. In other examples, the magnetic material can have a height of from 0.5 mm to 1.5 mm. In additional examples, the magnetic material can have an outer diameter of from about 1 mm to about 5 mm. In some other examples, the magnetic material can have an outer diameter of from about 1.5 mm to about 4 mm. In examples where the magnetic material is an annular body, the magnetic material can have a variety of inner diameters. In some specific examples, the magnetic material can have an inner diameter of from about 0.5 mm to about 3 mm. In other examples, the magnetic material can have an inner diameter of from about 0.8 to about 2.5 mm.

It is further noted that, while hydrogel sensor devices are illustrated in isolation (i.e. including only a single crosslinked hydrogel body or stack and associated support post(s)) in the figures, this is not to be construed as limiting. Individual hydrogel sensor devices can be combined in an array to provide a hydrogel sensor array. The hydrogel sensor array can be arranged in a variety of configurations, such as a 5×5 array, a 10×10 array, a 20×20 array, a 50×50 array, a 100×100 array, or the like. It is further noted, that individual hydrogel sensors within the array can be configured with a plurality of types of detectors, a plurality of types of crosslinked hydrogel bodies, etc., as desired, to increase the number and types of data points generated from the array.

The present disclosure also describes methods of manufacturing hydrogel sensor devices. Generally, the methods of manufacturing hydrogel sensor devices can include preparing a crosslinked hydrogel body which changes in volume in response to an environmental stimulus, positioning the crosslinked hydrogel network adjacent to a support post which mechanically supports the crosslinked hydrogel body during the change in volume, and positioning a sensor to detect the change in volume of the crosslinked hydrogel body.

In further detail, the crosslinked hydrogel body can be prepared to have a geometric shape that is suitable for fast response times. As described above, this can refer to preparing a crosslinked hydrogel body having a relatively high S/V, such as greater than about 3 mm$^{-1}$, for example. The crosslinked hydrogel body can be suitably shaped using a variety of techniques. For example, the crosslinked hydrogel body can be shaped by molding, cutting (e.g. laser cutting), the like, or a combination thereof. In some specific examples, the crosslinked hydrogel body can be hollow. The hollow channel can be formed before or after formation of the crosslinked hydrogel body or crosslinked hydrogel body stack. Where a hydrogel body stack is employed, other components of the stack can be similarly shaped by molding, cutting, the like, or a combination thereof.

In some examples, hydrogel interfacing layers can be positioned between crosslinked hydrogel bodies, the support base, a magnetic material, the like, or a combination thereof. In some specific examples, the hydrogel-interfacing layers can be adhered to one or more interfacing components using an adhesive or polymeric material. The surfaces of hydrogel-interfacing layers may be pre-treated to enhance adhesion to interfacing compounds. In some examples, the pre-treatment can be oxygen plasma treatment, mechanical surface roughening techniques, chemical surface activation. In some examples, UV activated adhesive, thermal activated adhesive or epoxies can be used to as the interfacing compound.

In some examples, the support post can be formed integrally with the support base, such as via a molding process. In other examples, the support post can be formed separately from the support base and connected to the support base, such as via a machining process, adhesives, fasteners, the like, or a combination thereof.

The crosslinked hydrogel body can be positioned adjacent to the support post to provide mechanical support to the crosslinked hydrogel body. However, the support post can be positioned relative to the crosslinked hydrogel body so as to not interfere, or minimally interfere, with the volume change of the crosslinked hydrogel body.

The sensor can be positioned in a variety of locations, depending on the particular sensor employed and the application of the hydrogel sensor device. In some examples, the sensor can be positioned on a side of the support base opposite the crosslinked hydrogel body. In some examples, the sensor can be positioned within the support base. In some examples, the sensor can be positioned within the support post. In some examples, the sensor can be positioned on the same side of the support base as the crosslinked hydrogel body. In some examples, a plurality of sensors can be employed. Where this is the case, one or more sensors can be positioned on a side of the support base opposite the crosslinked hydrogel body, within the support base, within the support post, on the same side of the support base as the crosslinked hydrogel body, or a combination thereof.

The present disclosure also describes methods of detecting an environmental stimulus. Generally, the methods of detecting an environmental stimulus can include preparing a crosslinked hydrogel body configured to change in volume in response to an environmental stimulus, positioning the crosslinked hydrogel network adjacent to a support post configured to mechanically support the crosslinked hydrogel body during the change in volume, and detecting the change in volume using a sensor.

As described above, the crosslinked hydrogel body can change in volume in response to an environmental stimulus, such as a presence or absence of a target molecule, temperature, pH, light, ultrasonic radiation, magnetic field, electric field, ionic strength, the like, or a combination thereof. As such, the hydrogel sensor devices described herein can be incorporated into a variety of bioreactors, or other suitable devices, where it is desirable to monitor one or more such environmental stimuli. Thus, the crosslinked hydrogel body can be exposed to the environmental stimulus, or environmental stimuli, to induce detectable changes in volume of the crosslinked hydrogel body. These changes in volume can be used to measure or quantify the environment stimulus or stimuli.

Depending on the particular application of the hydrogel sensor device, data points can be collected at a variety of time points to determine a current status of the environmental stimulus at a given time point, a rate of change of the environmental stimulus, etc. The specific periodicity or frequency at which the data points are collected can be optimized based on a particular application.

In some specific examples, environmental stimulus data can be transmitted to a remote device, such as a computer, a server (e.g. local data server, cloud server, etc.), a smart device, or the like for evaluation and monitoring by an end user or for data storage. In some examples, the hydrogel sensor device can be physically connected to the remote device using wires or the like. In other examples, the hydrogel sensor device can be wirelessly connected to the remote device. Where this is the case, a variety of suitable wireless protocols can be employed to transmit the environmental stimulus data to the remote device. Non-limiting examples can include Bluetooth® (e.g. Bluetooth® low energy (LE)), Zigbee, other suitable IEEE protocols, WiFi, WiMAX®, the like, or other suitable wireless protocols.

In some further examples, the environmental stimulus data can be processed by the remote device and the remote device can transmit instructions to a controller module of the bioreactor, or other suitable device, to alter and/or maintain one or more parameters, such as temperature, mixing rate, pH, osmolarity, etc. In some specific examples, the remote device can include a controller module of the bioreactor, or other suitable device. Thus, in some examples, the environmental stimulus data can be used to generate an automatic feedback response.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A hydrogel sensor device, comprising:
   a crosslinked hydrogel body which changes in volume in response to an environmental stimulus;
   a support post positioned to mechanically support the crosslinked hydrogel body during the change in volume, wherein the crosslinked hydrogel body is unbounded and the crosslinked hydrogel body circumscribes the support post; and
   a sensor positioned to detect the change in volume in the crosslinked hydrogel body, wherein the sensor comprises an optical detector, a magnetometer, an ultrasonic detector, an electrical inductor, or a combination thereof.

2. The hydrogel sensor device of claim 1, wherein the crosslinked hydrogel body has an exposed surface to volume (S/V) ratio of at least 3.0 mm$^{-1}$.

3. The hydrogel sensor device of claim 1, wherein the crosslinked hydrogel body comprises a plurality of stacked crosslinked hydrogel bodies.

4. The hydrogel sensor device of claim 3, wherein individual crosslinked hydrogel bodies of the plurality of stacked crosslinked hydrogel bodies are positioned between corresponding hydrogel interface layers.

5. The hydrogel sensor device of claim 1, wherein the support post is coupled to a support base.

6. The hydrogel sensor device of claim 5, wherein the sensor is incorporated into the support base.

7. The hydrogel sensor device of claim 5, further comprising a base-interface layer positioned between the crosslinked hydrogel body and the support base.

8. The hydrogel sensor device of claim 1, wherein the support post is rigid and non-electrically conductive.

9. The hydrogel sensor device of claim 1, wherein the sensor comprises a magnetometer, an electrical inductor, or a combination thereof.

10. The hydrogel sensor device of claim 9, wherein the sensor is a magnetic sensor which comprises a magnetometer and a magnetic material is disposed mechanically adjacent to the hydrogel body so as to move in response to the change in volume.

11. The hydrogel sensor device of claim 10, wherein the magnetometer is embedded within the support post.

12. The hydrogel sensor device of claim 10, wherein the magnetometer is positioned adjacent the support post.

13. The hydrogel sensor device of claim 10, wherein the magnetic material comprises at least one magnetic body.

14. The hydrogel sensor device of claim 13, wherein the at least one magnetic body is a permanent annular body slidably engaged over the support post.

15. The hydrogel sensor device of claim 10, further comprising a magnet-interface layer positioned between the magnetic material and the crosslinked hydrogel body.

16. The hydrogel sensor device of claim 15, wherein the magnet-interface layer comprises a polymer which is bonded to both the magnetic material and the crosslinked hydrogel body.

17. The hydrogel sensor device of claim 10, wherein the magnetic material comprises magnetic particles embedded within a hydrogel-interface layer.

18. The hydrogel sensor device of claim 10, wherein the magnetic material moves parallel to a plane of the magnetic sensor.

19. A method of manufacturing a hydrogel sensor device as in claim 1, comprising:
  preparing the crosslinked hydrogel body configured to change in volume in response to the environmental stimulus;
  positioning the crosslinked hydrogel network adjacent to and circumscribing the support post configured to mechanically support the crosslinked hydrogel body during the change in volume; and
  positioning the sensor to detect the change in volume in the crosslinked hydrogel body.

20. The method of claim 19, wherein preparing the crosslinked hydrogel body comprises molding, cutting, or a combination thereof.

21. The method of claim 19, wherein positioning the crosslinked hydrogel network comprises circumscribing the support post with the crosslinked hydrogel network.

* * * * *